US012784311B2

(12) United States Patent
Rajagopal et al.

(10) Patent No.: US 12,784,311 B2
(45) Date of Patent: Nov. 3, 2026

(54) FUSION OF DEEP-LEARNING BASED IMAGE RECONSTRUCTION WITH NOISY IMAGE MEASUREMENTS

(71) Applicants: The Regents of the University of California, Oakland, CA (US); The United States Government as Represented by the Department of Veterans Affairs, Washington, DC (US)

(72) Inventors: Abhejit Rajagopal, San Francisco, CA (US); Nicholas Dwork, San Francisco, CA (US); Peder E.Z. Larson, San Francisco, CA (US); Thomas A Hope, San Francisco, CA (US)

(73) Assignees: The Regents of the University of California, Oakland, CA (US); The United States Government as Represented by The Department of Veterans Affairs, Washington, DC (US)

( * ) Notice: Subject to any disclaimer, the term of this patent is extended or adjusted under 35 U.S.C. 154(b) by 222 days.

(21) Appl. No.: 18/720,866

(22) PCT Filed: Dec. 15, 2022

(86) PCT No.: PCT/US2022/081683
§ 371 (c)(1),
(2) Date: Jun. 17, 2024

(87) PCT Pub. No.: WO2023/114923
PCT Pub. Date: Jun. 22, 2023

(65) Prior Publication Data

US 2025/0069290 A1 Feb. 27, 2025

Related U.S. Application Data

(60) Provisional application No. 63/290,772, filed on Dec. 17, 2021.

(51) Int. Cl.
*G06T 12/20* (2026.01)
*G06T 5/60* (2024.01)
(Continued)

(52) U.S. Cl.
CPC ................ *G06T 12/20* (2026.01); *G06T 5/60* (2024.01); *G06T 11/60* (2013.01); *G06T 12/10* (2026.01);
(Continued)

(58) Field of Classification Search
CPC . G06T 12/20; G06T 5/60; G06T 11/60; G06T 12/10; G06T 2207/20081;
(Continued)

(56) References Cited

U.S. PATENT DOCUMENTS

2007/0047838 A1 3/2007 Milanfar et al.
2012/0027281 A1 2/2012 Jang et al.
(Continued)

OTHER PUBLICATIONS

Bhadra et al., "Medical image reconstruction with image-adaptive priors learned by use of generative adversarial networks." Retrieved on 22.02.203. Retrieved from https://arxiv.org/pdf/2001.10830.pdf.
(Continued)

*Primary Examiner* — Abhishek Sarma
(74) *Attorney, Agent, or Firm* — Kilpatrick Townsend & Stockton LLP

(57) ABSTRACT

The present disclosure relates to techniques for fusing deep learning-based image reconstructions with noisy image measurements with provable assurances that the resulting improved image does not remove the information content of the original noisy measurements or image. Particularly, aspects are directed to obtaining measurement data from an imaging modality, generating a base image by solving an optimization problem using at least a signal model and the measurement data, generating, using a deep-learning model,
(Continued)

a predicted image based on the measurement data, selecting a modified operator based on the signal model, generating an enhanced image by solving the modified optimization problem using at least: (i) the base image or the measurement data, (ii) the signal model, (iii) the predicted image, and (iv) the modified operator, and outputting the enhanced image.

20 Claims, 9 Drawing Sheets

(51) Int. Cl.

| | |
|---|---|
| ***G06T 11/60*** | (2026.01) |
| ***G06T 12/10*** | (2026.01) |
| ***G06V 10/764*** | (2022.01) |
| ***G16H 50/20*** | (2018.01) |

(52) U.S. Cl.

CPC .......... *G06V 10/764* (2022.01); *G16H 50/20* (2018.01); *G06V 2201/07* (2022.01)

(58) Field of Classification Search

CPC ..... G06T 2207/20084; G06T 2211/424; G06T 2211/441; G06V 10/764; G06V 2201/07; G16H 50/20

See application file for complete search history.

(56) References Cited

U.S. PATENT DOCUMENTS

| | | | |
|---|---|---|---|
| 2014/0327674 | A1 | 11/2014 | Sorkine-Hornung et al. |
| 2015/0049930 | A1 | 2/2015 | Brown |
| 2017/0039706 | A1 | 2/2017 | Mikhno et al. |

OTHER PUBLICATIONS

PCT/US2022/081683, International Search Report and Written Opinion, Mar. 16, 2023, 13 pages.

Wang et al., "Variational based Mixed Noise Removal with CNN Deep Learning Regularization," Retrieved on Feb. 22, 2023. Retrieved from https:/arxiv.org/pdf/1805.08094.pdf.

Xie et al., "Generative adversarial network based regularized image reconstruction for PET," Phys Med Biol.; 65(12). Retrieved on Feb. 22, 2023. Retrieved from https://www.ncbi.nlm.nih.gov/pmc/articles/PMC7413644/pdf/nlhms-1614189.pdf.

Low Dose (Simulated) FDG-PET

MR-derived Zero-Dose FDG-PET

Dichromatically-Interpolated FDG-PET

Full Dose FDG-PET

FUSION OF DEEP-LEARNING BASED IMAGE RECONSTRUCTION WITH NOISY IMAGE MEASUREMENTS

CROSS-REFERENCES TO RELATED APPLICATIONS

The present application is a national phase application claiming priority and benefit of International Pat. Appl. No. PCT/US2022/081683, filed on Dec. 15, 2022, which claims priority and benefit of U.S. Provisional Pat. Appl. No. 63/290,772, filed on Dec. 17, 2021, which are incorporated herein by reference in their entireties for all purposes

STATEMENT OF GOVERNMENT SUPPORT

This invention was made with government support under R01 AR074492, and R01 CA212148 awarded by the National Institutes of Health. The government has certain rights in the invention.

FIELD

The present disclosure relates to image reconstruction, and in particular to techniques for fusing deep learning-based image reconstructions with noisy image measurements with provable assurances that the resulting improved image does not remove the information content of the original noisy measurements or image.

BACKGROUND

Image reconstruction techniques are used to create 2-D and 3-D images from sets of 1-D projections. These reconstruction techniques form the basis for common imaging modalities such as computerized tomography (CT), magnetic resonance imaging (MRI), and positron emission tomography (PET), and they are useful in medicine, biology, earth science, archaeology, materials science, navigation, and nondestructive testing. The problem of reconstructing images from measurements at the boundary of a domain belong to the class of inverse problems. An inverse problem is the process of calculating from a set of observations the causal factors that produced them: for example, calculating an image in X-ray computed tomography, source reconstruction in acoustics, or calculating the density of the Earth from measurements of its gravity field. It is called an inverse problem because it starts with the effects and then calculates the causes. The historical mathematical foundation for solving such inverse problems include the Radon transform, the inverse Radon transform, and the projection slice theorem, central slice theorem or Fourier slice theorem. Computational techniques include analytical methods, such as filtered back-projection (FBP) and the inverse Fourier transform, and a variety of iterative reconstruction methods, such as Algebraic Reconstruction Technique (ART), iterative Sparse Asymptotic Minimum Variance algorithm, and statistical reconstruction based on models for the imaging system physics and, where appropriate, models for the sensor statistics.

More recently, artificial intelligence (AI) techniques such as deep-learning and neural networks, due to their success in tasks such as image classification, have emerged as a new tool for solving these inverse problems. The AI or machine-learning (ML) models used for image reconstruction (e.g., synthesis dictionaries, sparsifying transforms, tensor models, etc.) can be learned in various ways such as by using training datasets, or even learned jointly with the reconstruction, a setting called model-blind reconstruction or blind compressed sensing (BCS). While most of these methods perform offline reconstruction (where the reconstruction is performed once all the measurements are collected), recent works show that the models can also be learned in a time-sequential or online manner from streaming measurements to reconstruct dynamic objects. The learning can be done in an unsupervised manner employing model-based and surrogate cost functions, or the reconstruction algorithms (such as deep convolutional neural networks (CNNs)) can be trained in a supervised manner to minimize the error in reconstructing training datasets that typically include pairs of ground truth and undersampled data. In any event, the image reconstruction algorithms learn how to best do the reconstruction based on training from previous data, and, through this training procedure, aim to optimize the quality of the reconstruction.

SUMMARY

Deep-learning can provide enhanced reconstruction and denoising of imagery (such as CT, MRI, PET, and ultrasound), but can inadvertently leave out crucial details that are important for clinical interpretation and reading. A similar issue arises in non-medical imaging modalities including optical-RGB imagery, LiDAR, and radar, whereby the image reconstructed via deep-learning cannot be trusted. This present disclosure describes techniques for computing a fusion of deep learning image predictions together with the original measurements, with mathematically-provable assurances that the resulting improved image does not remove the information content of the original noisy measurements or image. As an example, the improvements in image quality in noisy (simulated low-dose) PET/MRI imagery are demonstrated herein using a deep learning network trained to predict PET directly from MRI without a radiation dose (i.e. synthetic PET). In this example, even though synthetic PET is missing patient-specific PET functional information, image quality is improved when combined with the original noisy PET image, and—crucially—functional information is retained.

In various embodiments, a computer-implemented method for image reconstruction is provided. The method includes: obtaining measurement data from one or more imaging modalities; generating a base image by solving an optimization problem using at least a signal model and the measurement data; generating, using a deep-learning model comprising model parameters learned for reconstruction of images, a predicted image based on the measurement data; selecting a modified operator based on physics, the signal model, or a system matrix; generating an enhanced image by solving a modified optimization problem using at least: (i) the base image or the measurement data, (ii) the signal model, (iii) the predicted image, and (iv) the modified operator; and outputting the enhanced image.

In some embodiments, the generating the base image comprises computing a solution to a image reconstruction problem using the signal model, the measurement data, and an unknown image to be reconstructed, computing a solution to a regularization function using the unknown image to be reconstructed, a reconstructed image, and a deep-learning derived image, comparing the solution to the image reconstruction problem and the solution to the regularization function, and determining the base image that satisfies or minimizes the optimization problem based on the comparing.

In some embodiments, the model parameters are learned, using a set of training data comprising a plurality of measurements associated with the one or more imaging modalities, based on minimizing a loss function.

In some embodiments, the generating the enhanced image comprises computing a solution to an image reconstruction problem using the base image or the measurement data, the signal model, the modified operator, and an unknown image to be reconstructed, computing a solution to a regularization function by comparing the image to be reconstructed to the predicted image and the measurement data, comparing the solution to the image reconstruction problem and the solution to the regularization function, and determining the enhanced image that satisfies or minimizes the modified optimization problem based on the comparing.

In some embodiments, the modified optimization problem is of the form:

$$\hat{x}_{enhanced} = \min_x \left|\tilde{A}x - \hat{x}_{conventional}\right| + R_{DL}(x, \hat{x}_{DL}, b)$$

where Ã is the modified operator, x is the image to be reconstructed, $\hat{x}_{conventional}$ is the base image or the measurement data, $R_{DL}$ is the regularization function, $\hat{x}_{DL}$ is the predicted image, and b is the measurement data.

In some embodiments, the meth of further comprises determining, by a user, a diagnosis or prognosis of a subject based on the enhanced image.

In some embodiments, the method further comprises detecting, characterizing, and/or classifying, by a data processing system, a tissue within the enhanced image.

In some embodiments, the base image is a noisy reconstructed positron emission tomography (PET) image, and the predicted image is a synthetic PET image.

In some embodiments, the method further comprises autonomously operating a vehicle based on the enhanced image.

In some embodiments, the base image is a noisy and sparse reconstructed LiDAR depth image, formed using a number of sensors, and the predicted image is a predicted depth image, reconstructed using deep learning on optical (RGB) images.

In some embodiments, the method further comprises autonomously operating a vehicle based on the enhanced image.

In some embodiments, the base image is a noisy and sparse reconstructed LiDAR depth image, formed using a number of sensors, and the predicted image is a predicted depth image, reconstructed using deep learning on optical (RGB) images.

In some embodiments, the method further comprises identifying an object in the enhanced image or classifying, by a machine-learning model, an object within the enhanced image.

In some embodiments, the base image is a noisy reconstructed image of buildings based on radar, and the predicted image is a predicted building mask, based on deep learning of optical imagery.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more data processors to perform part or all of one or more methods disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present disclosure is described in conjunction with the appended figures.

Figure 1:
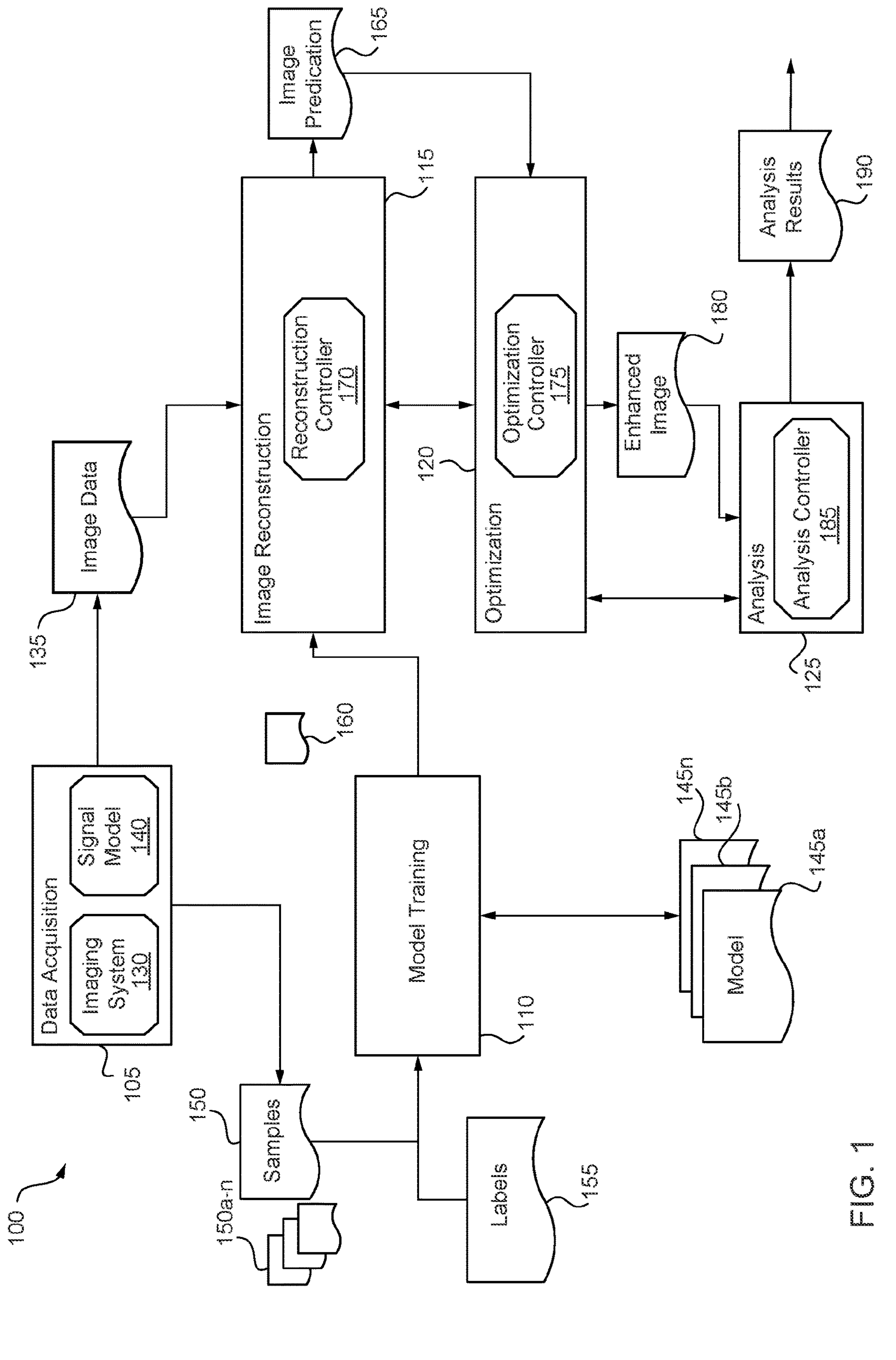
FIG. 1 shows an example computing environment for image reconstruction according to various embodiments.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Overview

The present disclosure describes techniques for image reconstruction. More specifically, embodiments of the present disclosure provide techniques for fusing deep learning-based image reconstructions with noisy image measurements with provable assurances that the resulting improved image does not remove the information content of the original noisy measurements or image. It should be understood that the examples and embodiments regarding CT, MRI, PET, and the like are described herein for illustrative purposes only and alternative modalities (e.g., optical-RGB imagery, LiDAR, and radar) will be suggested to persons skilled in the art for implementing various derived image reconstruction techniques in accordance with aspects of the present disclosure. Moreover, the use of any of these modalities for medical purposes can be modified (e.g., different tracers, angle configurations, wave lengths, etc.) to capture different structures or regions of objects for non-medical purposes (e.g., self-driving cars that utilize any combination of optical (RGB), LiDAR, and radar imagery; and 3-D reconstruction of buildings and terrain from airborne and satellite imagery, combining information from multiple sensors), and one or more of these modalities may be combined with one or more other modalities for implementing image reconstruction in accordance with aspects of the present disclosure. The result being that the techniques disclosed herein ensure that the image reconstruction can be trusted for use by both human and robotic operators.

Many image reconstruction problems take the form:

$$f(A, x) = b \qquad \text{(Equation 1)}$$

where x is the unknown image to be reconstructed, f(Ax) is the forward model, and b is the set of known (possibly noisy) measurements (e.g., sensor measurements such as spectral measurements).

The solution to such problems can be posed as an optimization problem:

$$\hat{x}_{conventional} = \min_x |f(Ax) - b| + R(x) \qquad \text{(Equation 2)}$$

where R(x) is a conventional regularization function, such as total-variation or a norm of a sparsity-inducing transform (e.g. wavelet).

Alternatively, deep-learning based reconstructions may produce an estimate $\hat{x}_{DL}$ without any regards to $\hat{x}_{conventional}$.

Although the use of deep-learning techniques is beneficial in image reconstruction, and achieves significant improvements compared with traditional analytical and iterative reconstruction based approaches, image reconstruction is still challenging when it comes to noisy measurements, which are particularly prevalent in 3-D image modalities such as CT, MRI, and PET imaging. One of these challenges is reliability of the reconstructed image to retain relevant information content from the original image or measurements. Specifically, conventional deep-learning based image reconstructions are sometimes unreliable in various settings (e.g., clinical or operational settings) because they can inadvertently disregard or all together remove relevant information content (e.g., clinically or operationally relevant image content such as pathology or sensor data), especially if the deep-learning model is not properly designed or the particular information content (e.g., pathology or sensor data) is not present in the training data used to develop the deep-learning model.

To address these limitations and problems, the techniques for image reconstruction of the present embodiments combine deep-learning image predictions with the original noisy measurements to improve accuracy without ignoring or removing relevant information content. The techniques described in detail herein take the output of the deep-learning image predictions $\hat{x}_{DL}$ and fuses that with the conventional reconstruction $\hat{x}_{conventional}$ (or alternatively the raw measurement data b) using an optimization approach. This allows for the incorporation of information from the deep-learning image prediction $\hat{x}_{DL}$ into the conventional reconstruction $\hat{x}_{conventional}$ or raw measurement data b in such a manner (constrained by the optimization approach) that the final image output is assured to be consistent with the raw measurement data b.

The optimization approach for the fusion of the deep-learning image prediction $\hat{x}_{DL}$ and the conventional reconstruction $\hat{x}_{conventional}$ (or alternatively the raw measurement data b) is implemented by solving a modified optimization problem of the form:

$$\hat{x}_{enhanced} = \min_x |\tilde{A}x - \hat{x}_{conventional}| + R_{DL}(x, \hat{x}_{DL}, b) \qquad \text{(Equation 3)}$$

where $\tilde{A}$ is a modified operator (e.g., a down sampling and smoothing operator) determined based on the physics of the problem, a signal model such as a noise model, or system matrix (e.g., Equation 1), x is the image to be reconstructed, $\tilde{A}$ is applied to x, which should optimally match the conventional reconstruction $\hat{x}_{conventional}$ (or alternatively the raw measurement data b), and $R_{DL}$ (x, $\hat{x}_{DL}$, b), which computes a regularization term comparing the image to be reconstructed x to the deep-learning image prediction $\hat{x}_{DL}$ and the raw measurement data b. The regularization term may be implemented using various techniques including gradient matching, sparsity pattern matching, joint sparsity, joint total variation, and the like. An important aspect being that in conventional approaches the deep-learning image prediction $\hat{x}_{DL}$ was not used as a modality for the reconstruction and regularization much less in combination with the conventional reconstruction $\hat{x}_{conventional}$. The final output $\hat{x}_{enhanced}$ is the image to be reconstructed x that satisfies or minimizes the modified optimization problem. Therefore, as long as the term: $\tilde{A}x - \hat{x}_{conventional} = 0$ then an image to be reconstructed x has been found that is physically consistent with the raw measurement data b and, in addition, the image to be reconstructed x has been regularized via the term: $R_{DL}$(x, $\hat{x}_{DL}$, b) (e.g., minimizes the regularization term). Consequently, by careful choice of $\tilde{A}$, improvements can be made in the image quality of $\hat{x}_{enhanced}$ over $\hat{x}_{conventional}$ by borrowing information from the unreliable prior estimate $\hat{x}_{DL}$.

In the examples described in detail herein, it is demonstrated that combining of the deep-learning image predictions with the original noisy measurements improves accuracy of the image reconstruction in a medical setting where:

$\hat{x}_{conventional}$ is a noisy reconstructed PET image $\hat{x}_{DL}$ is a synthetic PET image (predicted without using measurements b).

However, the techniques described herein for combining of the deep-learning image predictions with the original noisy measurements also apply to many other modalities, for example:

For self-driving cars:

$\hat{x}_{conventional}$ is a noisy and sparse reconstructed LiDAR depth image, formed using a limited number of sensors $\hat{x}_{DL}$ is a predicted depth image, reconstructed using deep learning on optical (RGB) images For satellite-based 3D reconstruction:

$\hat{x}_{conventional}$ is a noisy reconstructed image of buildings based on radar $\hat{x}_{DL}$ is a predicted building mask, based on deep learning of optical imagery There are many variations using different modalities and scenarios where one or more of these modalities may be degraded, and one or more data products may be generated using deep-learning.

One illustrative embodiment of the present disclosure is directed to a method that includes obtaining measurement data from one or more imaging modalities; generating a base image by solving an optimization problem using at least a signal model and the measurement data; inputting the measurement data into a deep-learning model comprising model parameters learned for reconstruction of images; generating, using the deep-learning model, a predicted image based on the measurement data; selecting a modified operator based on physics of the image reconstruction problem, the signal model, or system matrix; inputting: (i) the base image or the measurement data, (ii) the signal model, (iii) the predicted image, and (iv) the modified operator, into a modified optimization problem; generating an enhanced image by solving the modified optimization problem using at least: (i) the base image or the measurement data, (ii) the signal model, (iii) predicted image, and (iv) the modified operator; and outputting the enhanced image.

The generating of the base image may comprise computing a solution to a image reconstruction problem using the signal model, the measurement data, and an unknown image to be reconstructed, computing a solution to a regularization function using the unknown image to be reconstructed (e.g., computing a regularization function value using the unknown image to be reconstructed, a reconstructed image such as a conventional reconstructed image, and a deep-learning derived image), comparing the solution to the image reconstruction problem and the solution to the regularization function, and determining the base image that satisfies or minimizes the optimization problem based on the comparing.

The generating of the enhanced image may comprise computing a solution to an image reconstruction problem using the base image or the measurement data, the signal model, the modified operator, and an unknown image to be reconstructed, computing a solution to a regularization function by comparing the image to be reconstructed to the predicted image and the measurement data, comparing the solution to the image reconstruction problem and the solution to the regularization function, and determining the enhanced image that satisfies or minimizes the modified optimization problem based on the comparing.

Advantageously, these techniques provide for the ability to: robustly retain information content in the original image or measurements; use any deep-learning based image reconstruction algorithm, including any existing approach to denoise images or approaches utilizing the raw non-image measurements (e.g. k-space or sinograms); and provide overall improvements in image quality. Additionally, these techniques ensure that the resulting image reconstruction can be trusted for use by both human and robotic operators. For example, since these techniques improve on reliability in the image reconstruction, the techniques also improve on the intelligence that may be discerned from the image, e.g., for monitoring of disaster zones, or for civilian applications involving business analytics, or for medical diagnosis of patients.

Definitions

As used herein, when an action is "based on" something, this means the action is based at least in part on at least a part of the something.

As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

As used herein, a "signal modeling" refers to the task of describing a signal with respect to an underlying structure—a model of the signal's fundamental behavior. Analysis is the process of fitting such a model to a particular signal, and synthesis is the process by which a signal (e.g., an image) is reconstructed using the model and the analysis of data.

As used herein, a "image reconstruction" refers to a process that generates images from measurement data (e.g., x-ray absorption and projection data).

As used herein, "deep-learning" refers to a class of machine learning algorithms that uses multiple layers to progressively extract higher-level features from the raw input. For example, in image processing, lower layers may identify edges, while higher layers may identify the features relevant to an object or subject such as digits or letters or surface texture or body parts.

Systems for Fusing Deep-Learning Based Image Reconstructions with Noisy Image Measurements FIG. 1 illustrates an example computing environment 100 (i.e., a data processing system) for image reconstruction using a multi-stage reconstruction network according to various embodiments. As shown in FIG. 1, the image reconstruction performed by the computing environment 100 in this example includes several stages: a data acquisition stage 105, a deep-learning model training stage 110, a deep-learning image reconstruction stage 115, an image optimization stage 120, and an analysis stage 125.

The data acquisition stage 105 includes one or more imaging systems 130 (e.g., an MRI imaging system) for obtaining images 135 (e.g., MR images) of a subject or object. The imaging systems 130 are configured to use one or more imaging techniques such as CT, MRI, PET, optical-RGB imagery, LiDAR, radar, and the like to obtain the images 135. The imaging systems 130 are able to determine the difference between various structures and functions within the subject based on raw data measurements (e.g., x-ray absorption, water content, fluid characteristics, ranges of distances (e.g., variable distances), Doppler effect, and the like) associated with each of the imaging systems 130 and generate via signal modeling a series of two-dimensional images. The signal modeling being performed using one or more models of the signal's fundamental behavior (signal models 140). Once the series of two-dimensional images are collected by the scanner's computer, the two-dimensional images can be digitally "stacked" together by computer analysis to reconstruct a three-dimensional image of the subject/object or a portion of the subject/object. The two-dimensional images and/or the reconstructed three-dimensional images 135 (described herein as the conventional reconstruction) allow for easier identification and location of basic structures (e.g., organs). Each two-dimensional image and/or the reconstructed three-dimensional image 135 may correspond to a session time and a subject/object and depict an interior region of the subject/object. Each two-dimensional image and/or the reconstructed three-dimensional image 135 may further be of a standardized size, resolution, and/or magnification.

The deep-learning model training stage 110 builds and trains one or more deep-learning models 145*a*-145*n* ('n' represents any natural number)(which may be referred to herein individually as a model 145 or collectively as the models 145) to be used by the other stages for image reconstruction. The model 145 can be a machine-learning ("ML") model, such as a convolutional neural network ("CNN"), e.g. an inception neural network, a residual neural network ("Resnet"), a U-Net, a V-Net, a single shot multibox detector ("SSD") network, or a recurrent neural network ("RNN"), e.g., long short-term memory ("LSTM") models or gated recurrent units ("GRUs") models, or any combination thereof. The model 145 can also be any other suitable ML model trained in image reconstruction, such as a three-dimensional CNN ("3DCNN"), a dynamic time warping ("DTW") technique, a hidden Markov model ("HMM"), etc., or combinations of one or more of such techniques—e.g., CNN-HMM or MCNN (Multi-Scale Convolutional Neural Network). The computing environment 100 may employ the same type of model or different types of models for image reconstruction.

To train a model 140 in this example, samples 150 are generated by acquiring digital images, splitting the samples into a subset of samples 150*a* for training (e.g., 90%) and a subset of samples 150*b* for validation (e.g., 10%), preprocessing the subset of samples 150*a* and the subset of samples 150*b*, optionally augmenting the subset of samples 150*a*, and in some instances annotating the subset of samples 150*a* with labels 155. The subset of samples 150*a* are acquired from one or more modalities (e.g., CT, MRI, PET, optical-RGB imagery, LiDAR, radar, and the like). In some instances, the subset of samples 150*a* are acquired from a data storage structure such as a database, an image system (e.g., one or more imaging systems 130), or the like associated with the one or more modalities. The samples 150 include the raw measurement data such as x-ray absorption, water content, fluid characteristics, ranges of distances (e.g., variable distances), Doppler effect, and the like from the modalities. In some instances, the samples 150 include the two-dimensional images and/or the reconstructed three-dimensional images 135 generated from the raw measurement data.

The splitting may be performed randomly (e.g., a 90/10% or 70/30%) or the splitting may be performed in accordance with a more complex validation technique such as K-Fold Cross-Validation, Leave-one-out Cross-Validation, Leave-one-group-out Cross-Validation, Nested Cross-Validation, or the like to minimize sampling bias and overfitting. The preprocessing may comprise cropping the images such that each image only contains a single object of potential interest. In some instances, the preprocessing may further comprise standardization or normalization to put all features on a same scale (e.g., a same size scale or a same color scale or color saturation scale). In certain instances, the images are resized with a minimum size (width or height) of predetermined pixels (e.g., 2500 pixels) or with a maximum size (width or height) of predetermined pixels (e.g., 3000 pixels) and kept with the original aspect ratio.

Augmentation can be used to artificially expand the size of the subset of samples 150*a* by creating modified versions of samples in the datasets. Image data augmentation may be performed by creating transformed versions of images in the datasets that belong to the same class as the original image. Transforms include a range of operations from the field of image manipulation, such as shifts, flips, zooms, and the like. In some instances, the operations include random erasing, shifting, brightness, rotation, Gaussian blurring, and/or elastic transformation to ensure that the model 145 is able to perform under circumstances outside those available from the subset of samples 150*a* (generalization).

Annotation can be performed manually by one or more humans (annotators such as radiologists or pathologists) confirming characteristics of each sample of the subset of samples 150*a* and providing labels 155 to the samples. In some instances, a subset of samples 150 may be transmitted to an annotator device to be included within a training data set (i.e., the subset of samples 150*a*). Input may be provided (e.g., by a radiologist) to the annotator device using (for example) a mouse, track pad, stylus and/or keyboard that indicates (for example) the ground truth image, signal model, system matrix, and/or sensor measurements to be used for reconstructing the image. Annotator device may be configured to use the provided input to generate labels 155 for each sample. For example, the labels 155 may include the ground truth image, signal model, system matrix, and/or sensor measurements. For the samples, which are annotated by multiple annotators, the labels from all annotators may be used. In some instances, annotation data may further indicate a type of an object of potential interest. For example, if an object of potential interest is an organ, then annotation data may indicate a type of organ or tissue, such as a liver, a lung, a pancreas, and/or a kidney.

The training process for model 145 includes selecting hyperparameters for the model 145 and performing iterative operations of inputting samples from the subset of samples 150*a* into the model 140 to find a set of model parameters (e.g., weights and/or biases) that minimizes a cots function such as loss or error function for the model 145. The hyperparameters are settings that can be tuned or optimized to control the behavior of the model 145. Most models explicitly define hyperparameters that control different aspects of the models such as memory or cost of execution. However, additional hyperparameters may be defined to adapt a model to a specific scenario. For example, the hyperparameters may include the number of hidden units of a model, the learning rate of a model, the convolution kernel width, or the number of kernels for a model. The cost function can be constructed to measure the difference between the outputs inferred using the models 145 (the deep-learning image prediction) and the ground truth annotated to the samples using the labels 155. For example, high noise sonogram data may be input through the model 145 and the output image may be compared to a low noise image (ground truth) constructed from the sonogram data. These two images may be compared across multiple parameters such as image noise, low contrast resolution, low contrast detectability, noise texture, and the like. The output image reports the differences to the network via backpropagation which trains and strengthens the model 145 based on the desired output.

Once the set of model parameters are identified, the model 145 has been trained and can be validated using the subset of samples 150*b* (testing or validation data set). The validation process includes iterative operations of inputting samples from the subset of samples 150*b* into the model 145 using a validation technique such as K-Fold Cross-Validation, Leave-one-out Cross-Validation, Leave-one-group-out Cross-Validation, Nested Cross-Validation, or the like to tune the hyperparameters and ultimately find the optimal set of hyperparameters. Once the optimal set of hyperparameters are obtained, a reserved test set of samples from the subset of samples 150*b* are input into the model 145 to obtain output (the reconstructed image), and the output is evaluated versus ground truth images using correlation techniques such as Bland-Altman method and the Spearman's rank correlation coefficients and calculating performance metrics such as the error, accuracy, precision, recall, receiver operating characteristic curve (ROC), etc.

As should be understood, other training/validation mechanisms are contemplated and may be implemented within the computing environment 100. For example, the model 145 may be trained and hyperparameters may be tuned on samples from the subset of samples 150*a* and the samples from the subset of samples 150*b* may only be used for testing and evaluating performance of the model 145. Moreover, although the training mechanisms described herein focus on training a new model 145. These training mechanisms can also be utilized to fine tune existing models 145 trained from other datasets. For example, in some instances, a model 145 might have been pre-trained using samples from different modalities. In those cases, the models 145 can be used for transfer learning and retrained/validated using the samples 150.

The deep-learning model training stage 110 outputs trained models including one or more trained image reconstruction models 160. A deep-learning image prediction 165 is obtained by a reconstruction controller 170 using the image reconstruction models 160 within the deep-learning image reconstruction stage 115. For example, the reconstruction controller 170 executes processes for inputting measurement data from a modality (e.g., a CT scanner) into the image reconstruction models 160, generating, using the image reconstruction models 160, the deep-learning image prediction 165 (a reconstructed image) based on the measurement data from the modality, and obtaining the output of the deep-learning image prediction 165 from the image reconstruction models 160. The image reconstruction models 160 utilize one or more image reconstruction algorithms such as CNNs, automated transform by manifold approximation (AUTOMAP). Filtered back projection (FBP) algorithms, delay-guaranteed energy profile-aware routing (DEAR), python reconstruction operators in neural networks (PYRO-NN), Improved GoogLeNet, and the like order to extract statistical features and relationships used to predict the image.

The two-dimensional images and/or the reconstructed three-dimensional images 135 and/or the measurement data from a modality (e.g., a CT scanner), the signal model 140, and the deep-learning image prediction 165 are availed to an optimization controller 175 within the image optimization stage 120. An enhanced image 180 is generated by the optimization controller 175 based on the two-dimensional images and/or the reconstructed three-dimensional images 135 and/or the measurement data from a modality (e.g., a CT scanner), the signal model 140, and the deep-learning image prediction 165. Optimization controller 175 executes processes for the fusion of the deep-learning image prediction 165 and the two-dimensional images and/or the reconstructed three-dimensional images 135 and/or the measurement data by solving a modified optimization problem. In some instances, the modified optimization problem is in the form of Equation 3, where $\tilde{A}$ is a modified operator (e.g., a down sampling and smoothing operator) determined based on the signal model 140, x is the image to be reconstructed, $\tilde{A}$ is applied to x, which should optimally match the two-dimensional images and/or the reconstructed three-dimensional images 135 (or alternatively the measurement data), and $R_{DL}(x, \hat{x}_{DL}, b)$, which computes a regularization term comparing the image to be reconstructed x to the deep-learning image prediction 165 and the measurement data. The regularization term may be implemented using various techniques including gradient matching, sparsity pattern matching, joint sparsity, joint total variation, and the like. The final output enhanced image 180 is the image to be reconstructed x that satisfies or minimizes the modified optimization problem.

The enhanced image 180 may be transmitted to an analysis controller 185 within the analysis stage 125. The analysis controller 185 executes processes for obtaining or receiving the enhanced image 180 and determining analysis results 190 based on the enhanced image 180. In some instances, the analysis results 190 are classification of objects in the enhanced image 180. In some instances, the enhanced image 180 and/or the analysis results 190 are further used to determine a diagnosis and/or a prognosis for a subject. In other instances, the enhanced image 180 and/or the analysis results 190 are further used to determine an operation status for a machine such as a vehicle. In other instances, the enhanced image 180 and/or the analysis results 190 are further used to determine a status of an object within the enhanced image such as a movement change, size change, color change, or the like.

While not explicitly shown, it will be appreciated that the computing environment 100 may further include a developer device associated with a developer. Communications from a developer device to components of the computing environment 100 may indicate what types of input samples, measurement data, and/or images are to be used for the models, a number and type of models to be used, hyperparameters of each model, for example, learning rate and number of hidden layers, how data requests are to be formatted, which training data is to be used (e.g., and how to gain access to the training data) and which validation technique is to be used, and/or how the controller processes are to be configured.

Figure 2:
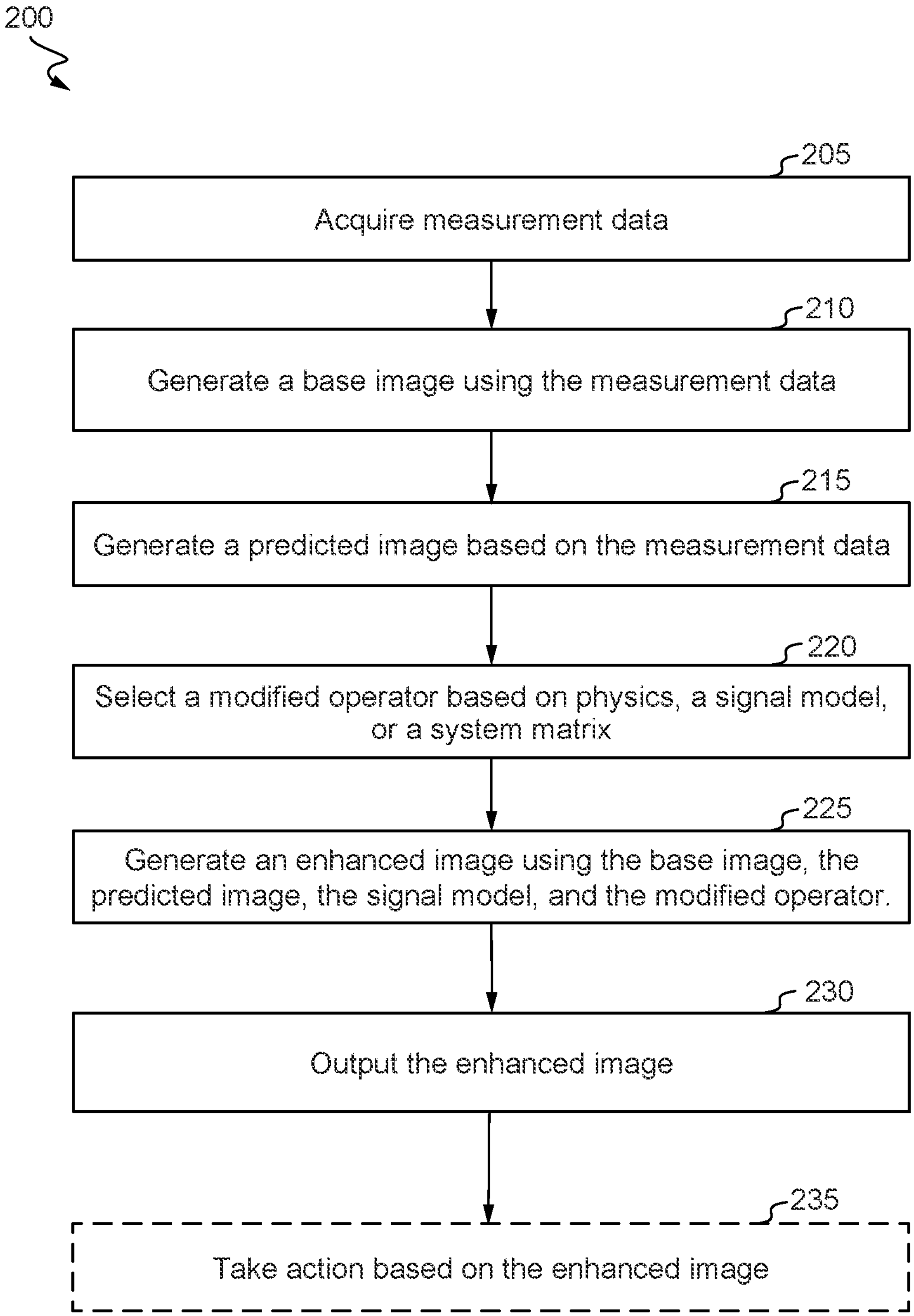
FIG. 2 shows a process for image reconstruction optimization according to various embodiments.

Techniques for Fusing Deep-Learning Based Image Reconstructions with Noisy Image Measurements FIG. 2 is a flowchart illustrating a process 200 for image reconstruction and optimization according to certain embodiments. The processing depicted in FIG. 2 may be implemented in software (e.g., code, instructions, program) executed by one or more processing units (e.g., processors, cores) of the respective systems, hardware, or combinations thereof. The software may be stored on a non-transitory storage medium (e.g., on a memory device). The method presented in FIG. 2 and described below is intended to be illustrative and non-limiting. Although FIG. 2 depicts the various processing steps occurring in a particular sequence or order, this is not intended to be limiting. In certain alternative embodiments, the steps may be performed in some different order or some steps may also be performed in parallel. In certain embodiments, such as in the embodiment depicted in FIG. 1, the processing depicted in FIG. 2 may be performed by image reconstruction models 160, reconstruction controller 170, optimization controller 175, and/or analysis controller 185 to generate enhanced images (and optionally analysis results).

Process 200 begins at block 205 where measurement data is obtained from one or more imaging modalities. The measurement data may include x-ray absorption, water content, fluid characteristics, ranges of distances (e.g., variable distances), Doppler effect, sensor data, and the like. The measurement data is generated using the one or more imaging modalities. For example, a user may operate one or more imaging systems that use the one or more medical imaging modalities to generate the measurement data, as discussed with respect to FIG. 1.

At block 210, the measurement data is input into an optimization problem and a base image is generated by solving the optimization problem using at least a signal model and the measurement data. In some instances, the generating the base image comprises computing a solution to a image reconstruction problem using the signal model, the measurement data, and an unknown image to be reconstructed, computing a solution to a regularization function using the unknown image to be reconstructed (e.g., computing a regularization function value using the unknown image to be reconstructed, a reconstructed image such as a conventional reconstructed image, and a deep-learning derived image), comparing the solution to the image reconstruction problem and the solution to the regularization function, and determining the base image that satisfies or minimizes the optimization problem based on the comparing. In some instances, the image reconstruction problem is in the form of Equation (1). In some instances, the optimization problem is in the form of Equation (2). In some instances, the optimization problem is in the form of Equation (2) and the image reconstruction problem is in the form of Equation (1).

At block 215, the measurement data is input into a deep-learning model comprising model parameters learned for reconstruction of images. The deep-learning model is used to generate a predicted image based on the measurement data. The model parameters are learned, using a set of training data comprising a plurality of measurements associated with the one or more imaging modalities, based on minimizing a loss function.

At block 220, a modified operator is selected based on physics of the image reconstruction problem, the signal model, a system matrix, or a combination thereof. In certain instances, the modified operator is selected based on the signal model.

At block 225, the base image or the measurement data, the signal model, the predicted image, and the modified operator are input into a modified optimization problem. An enhanced image is generated by solving the modified optimization problem using at least: (i) the base image or the measurement data, (ii) the signal model, (iii) predicted image, and (iv) the modified operator. The generating the enhanced image comprises computing a solution to an image reconstruction problem using the base image or the measurement data, the signal model, the modified operator, and an unknown image to be reconstructed, computing a solution to a regularization function by comparing the image to be reconstructed to the predicted image and the measurement data, comparing the solution to the image reconstruction problem and the solution to the regularization function, and determining the enhanced image that satisfies or minimizes the modified optimization problem based on the comparing. In some instances, the modified optimization problem is of the form Equation (3) where $\tilde{A}$ is the modified operator, x is the image to be reconstructed, $\hat{x}_{conventional}$ is the base image or the measurement data, $R_{DL}$ is the regularization function, $\hat{x}_{DL}$ is the predicted image, and b is the measurement data.

At block 230, the enhanced image is output. In some instances, the portion of the enhanced image is provided. For example, the enhanced image may be stored in a storage device, communicated to a user, and/or displayed on a user device.

At optional block 235, action is taken based on the enhanced image. In some instances, the action includes determining a diagnosis or prognosis of a subject based on the enhanced image. In other instances, the action includes detecting, characterizing, and/or classifying, by a data processing system, a tissue within the enhanced image (e.g., classifying, by a machine-learning model, a tissue within the enhanced image). For example, the base image may be a noisy reconstructed PET image, and the predicted image may be a synthetic PET image. In some instances, the action includes autonomously operating a vehicle based on the enhanced image. For example, the base image may be a noisy and sparse reconstructed LiDAR depth image, formed using a number of sensors, and the predicted image may be a predicted depth image, reconstructed using deep learning on optical (RGB) images. In some instances, the actions includes identifying an object in the enhanced image. In other instances, the action includes classifying, by a machine-learning model, an object within the enhanced image. For example, the base image may be a noisy reconstructed image of buildings based on radar, and the predicted image may be a predicted building mask, based on deep learning of optical imagery.

Examples

The systems and methods implemented in various embodiments may be better understood by referring to the following examples.

Introduction

The use of PET imaging for the localization and quantification of cancer and cancer therapy has grown over the years for use in neck-head, chest, and abdomen. Despite state-of-the-art detectors, currently PET imagery is significantly statistics- or count-limited. To increase the count, and thereby the signal-to-noise ratio (SNR), higher radiation doses must be injected into the patient, which can pose considerable risk, especially for pediatrics. This limitation often results in low-resolution and/or noisy 2D/3D PET imagery acquired clinically with lower doses. Note here the resolution and SNR are interrelated, as the SNR of a PET image can be improved by reducing the spatial resolution, although this may detract from the readability.

Consequently, there has been great interest in improving the resolution and SNR of PET imagery by incorporating additional information into the reconstruction or inversion model. Additional information reduces the uncertainty about the PET image to be recovered, by either increasing the fidelity of the existing measurements with respect to the assumed forward model, incorporating additional measurements that reduce the ill-posedness of the inverse problem, or both.

Besides detector improvements such as time-of-flight (ToF) PET, a traditional algorithmic approach to improving PET image reconstruction is to improve the accuracy of the 511-keV photon attenuation correction (μ-maps) of the subject (typically derived from either CT or MRI) used in the forward model. Recently, there has been a push for synthesizing μ-maps from MRI using deep learning, even though MRI does not directly measure electron density information of the subject volume, as this avoids administering an additional radiation dose (via CT) to the patient. Among other benefits, simultaneous PET/MRI can also solve many issues related to patient motion and can improve interpretation of PET imagery by providing excellent soft-tissue contrast.

To this end, there has been an increased focus on regularized reconstructions, including via compressed sensing or sparse coding objectives, to help constrain the PET/MR image reconstruction problem. For compressed sensing-type objectives, explicit regularization includes both sparsity and joint-sparsity terms $R(x)=\|\varphi x\|_p$, whereas implicit regularization can be achieved via sparse coding using a Deep Image Prior (DIP) technique. Both these methods are desirable over conventional direct deep learning reconstructions, which require high resolution exemplars for training and may suffer from data inconsistencies due to the feedforward projection scheme. One approach to correct this is to incorporate proximal gradient method iterative algorithms into the network architecture (e.g. loop unrolling), although the choice of network architecture (e.g. CNN-based or model-based) and regularization function remains open. Although such methods are theoretically compelling in comparison to black-box neural network techniques that may be unreliable in the presence of input perturbations or dataset-shift, trainable DNN-based optimization algorithms still lack performance guarantees.

Thus, besides investigating a new sparsity-based technique to improve the resolution and SNR of PET/MR imagery, aspects of the present disclosure are directed to a new principled way to incorporate deep learning predictions into well-studied model-based reconstruction algorithms, with strong performance and data consistency assurances. In particular, in this particular example it is demonstrated how an image-to-image neural network (domain translating T1-weighted 3D MRI to 3D PET imagery) can be combined with a signal equation (dichromatic interpolation) to improve the SNR (absolute error, relative error, structural similarity) of noisy low-dose PET/MR imagery, measured relative to a corresponding full-dose PET/MR.

This is notable because the neural network prediction of PET from MRI does not require a radiation dose to the patient, and thus the resulting synthetic PET image predicted by the network is crucially wrong in voxels where the functional information of PET cannot be predicted from the anatomical information of T1-weighted MRI. Still, the MR-based synthetic image serves a purpose when utilized with dichromatic interpolation, in providing higher-resolution information about the gradient of hidden (uncorrupted) PET image when—and only when-such information is ambiguous in the measured (noisy) PET imagery. This is an important feature of the approach described herein that assures improvements when utilizing deep learning predictions.

Methods

3D UNet for Domain Translation

Figure 3:
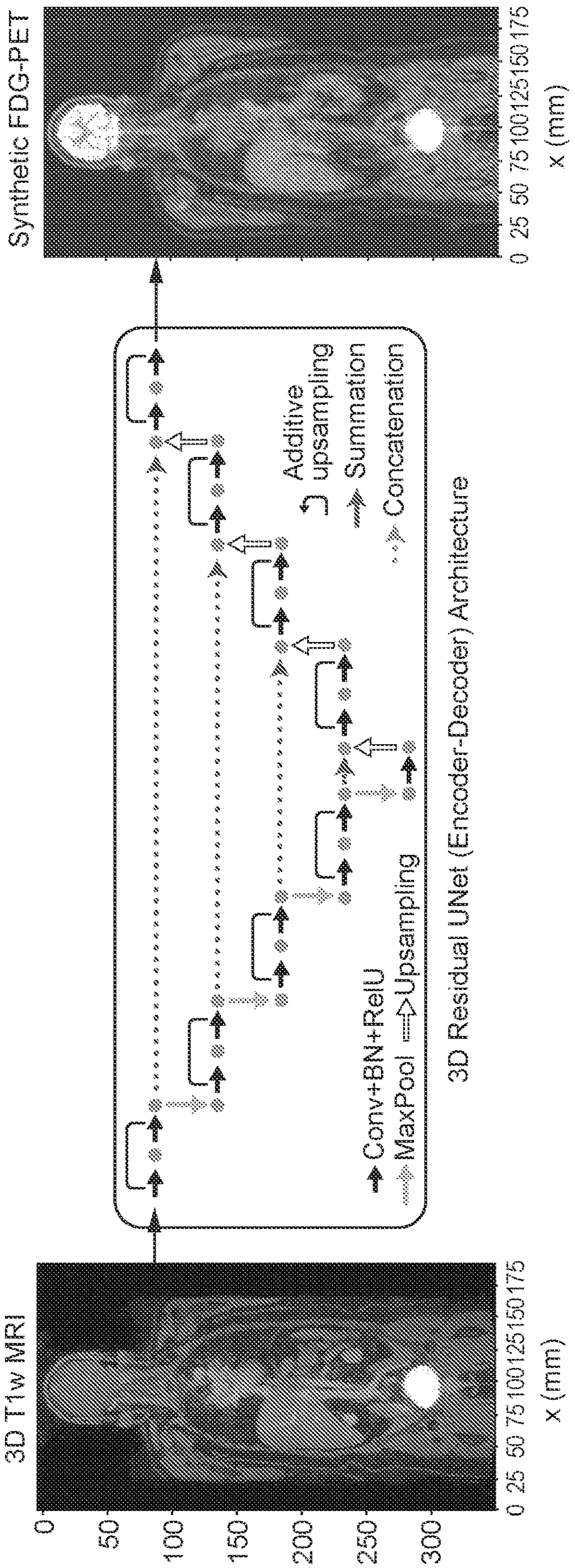
FIG. 3 shows a 3D residual UNet architecture according to various embodiments.

A 3D UNet with residual connections was used to predict PET physiological uptake from input MRI. Since the input MRI fundamentally does not contain all the information contained in a PET scan, this technique cannot be expected to fully predict PET uptake, and thus the term synthetic PET is used. The objective used for training the algorithm combines p-norm error (here we choose p=2) with a projection or line integral loss that acts as a perceptual loss for tomography, as:

$$\min_{\theta}\|x-f_\theta(z)\|_p+\lambda\|Px-Pf_\theta(z)\|_p \quad \text{Equation (4)}$$

where z is the input MRI (e.g. T1, T2, or Dixon water image), x is the groundtruth PET image (e.g. produced by conventional ToF-OSEM reconstruction[15]), $f_\theta$ is the domain translating 3D UNet, and P is a system/projection matrix so $P_x$ and $Pf_\theta(z)$ represent simulated sinograms. This training was performed offline on a dataset of 40 paired PET-MRI exams, and the network operation $f_\theta$ was fixed with optimal $\hat{\theta}$ prior to all subsequent steps. Post contrast T1-weighted MRI was used as input and full-dose 18F-FDG-PET/MRI as groundtruth. FIG. 3 shows the 3D residual UNet architecture takes an arbitrarily-sized T1-weighted volume (resampled to 1 mm isotropic resolution) and generates a corresponding synthetic 18F-FDG-PET volume of equal size and resolution.

Transferring Structure with Joint-Sparsity Regularization

The standard PET signal model is $y=Ax+\bar{r}$, where y is a set of measured PET sinograms, A is the system matrix, x is the true tracer distribution in image space, and r is random noise. Initially, take $\bar{r}=0$.

The conventional image reconstruction problem with compressed sensing can be written as:

$$\min_{x}\|Ax-y\|_p+\lambda\|\psi x\|_1 \quad \text{Equation (5)}$$

To transfer spatial structure from MRI or other high-resolution reference z, Equation 5 may be modified to:

$$\min_{x}\|Ax-y\|_p+\lambda\left\|[\psi x,\psi z]^T\right\|_1 \quad \text{Equation (6)}$$

to encourage the structure of the reconstructed image to match the structure of the reference z, unless this is in conflict with the the data-model consistency term. Joint-sparsity can be achieved by choosing Ψ as a spectral transform, or even more simply as the spatial gradient operator ∇, leading to what is called "joint total variation". Unfortunately, this approach has limited benefits when the structure and sparsity pattern of x and z do not overlap significantly, as is the case when MRI is used as a high-resolution anatomical reference/prior.

Instead, aspects of the present disclosure transfer structure by using a deep domain-translated PET prior $\tilde{x}=f_\theta(z)$, as:

$$\min_{x}\|Ax-y\|_p+\lambda\left\|[\psi x,\psi\tilde{x}]^T\right\|_1 \quad \text{Equation (7)}$$

As a practical note, this requires access to the true system matrix, which can sometimes be challenging to obtain.

Transferring Structure Via Dichromatic Interpolation

Another approach to incorporate structure, which can avoid the need to repeat the reconstruction process using the system matrix, is to utilize multi-modality interpolation. The multi-modality interpolation can be used to upsample a low-resolution image (e.g. downsampled to mitigate noise) using PET-domain-translated MRI, $\tilde{x}$, as a structural and statistically-representative template. The objective function in this case is:

$$\min_{x\in[0,1]} \|DBx - x_0\|_{Fr}^2 + \lambda\|\Delta x - \Delta\tilde{x}\|_{w,2}^2 \quad \text{Equation (8)}$$

where $x_0$ is the initial (conventionally-reconstructed) count-limited PET image, $\tilde{x}$ is the domain-translated synthetic PET image, x is the dichromatically interpolated/enhanced PET image, B is taken to be a blurring operator, D is a downsampling operator, w=1, and $\lambda$ is user-provided a Tikhonov-style regularization parameter. The idea here is that downsampling noisy PET imagery increases SNR at the expense of reducing resolution and contrast, but this can be recovered by borrowing gradient information from the synthetic PET image.

Solving the Optimization Problem

Equation (8) is a constrained least-squares problem, and its solution can be given by a number of convex solvers, including CVX. However, the interpolated image can be determined more efficiently with the Fast Iterative Shrinkage Threshold Algorithm (FISTA) by forming an equivalent optimization problem. A beneficial property of FISTA is that it exhibits convergence of $\mathcal{O}(1/k^2)$ where k is the iteration number, requiring fewer iterations than other methods for a given error. FISTA solves problems of the form:

$$\min_x F(x) + G(x) \quad \text{Equation (9)}$$

where in this case F and G are of the form:

$$F(x) = \|DBx - x_0\|_{Fr}^2 + \lambda\|\Delta x - \Delta\tilde{x}\|_{w,2}^2 \quad \text{Equation (10)}$$

$$G(x) = 1_{[0,1]}(x) \quad \text{Equation (11)}$$

where 1 is the element-wise indicator function of the [0, 1], taking value 0 when every element is within the interval and infinity otherwise. To improve the rate of convergence, FISTA was used with line search. The promximal operator of G, required by the algorithm, is a Euclidean projection onto the $[0, 1]^{N_H}$ set: $\text{prox}_{tG}(\bullet)=\min(\max(\bullet,0))$ for any t>0, where the max and min operations are performed on each component of the input vector individually.

Simulation of Low-dose PET Imagery

To evaluate quantitative improvements in PET/MRI reconstruction accuracy from noisy PET data, a low-dose 3D PET imagery dataset was simulated by sampling statistical distributions defined by images in a real, full-dose 18F-FDG-PET/MRI dataset (reconstructed with vendor-provided ToF-OSEM for two iterations), and additionally injecting various levels and types of noise in image-space. In particular, as radioactive decay follows a Poisson distribution, the amplitude of each voxel was used in a reconstructed PET image to define and sample a Poisson distribution with parameter $\lambda$. Although this technique assumes that the amplitude, a reconstructed voxel, is the "true" value, it has been shown that similar statistical distributions model noise in PET acquisition due to the effect of scattering and random coincidence events and also after reconstruction, e.g., using a negative binomial distribution with dispersion parameter a used to describe deviations from the Poisson distribution. Thus, this sampling technique can be applied as a simple surrogate for a full forward simulator. Moreover, sampling in the image-domain avoids the need to extract vendor-specific geometry information that can sometimes be difficult to obtain.

Figure 4:
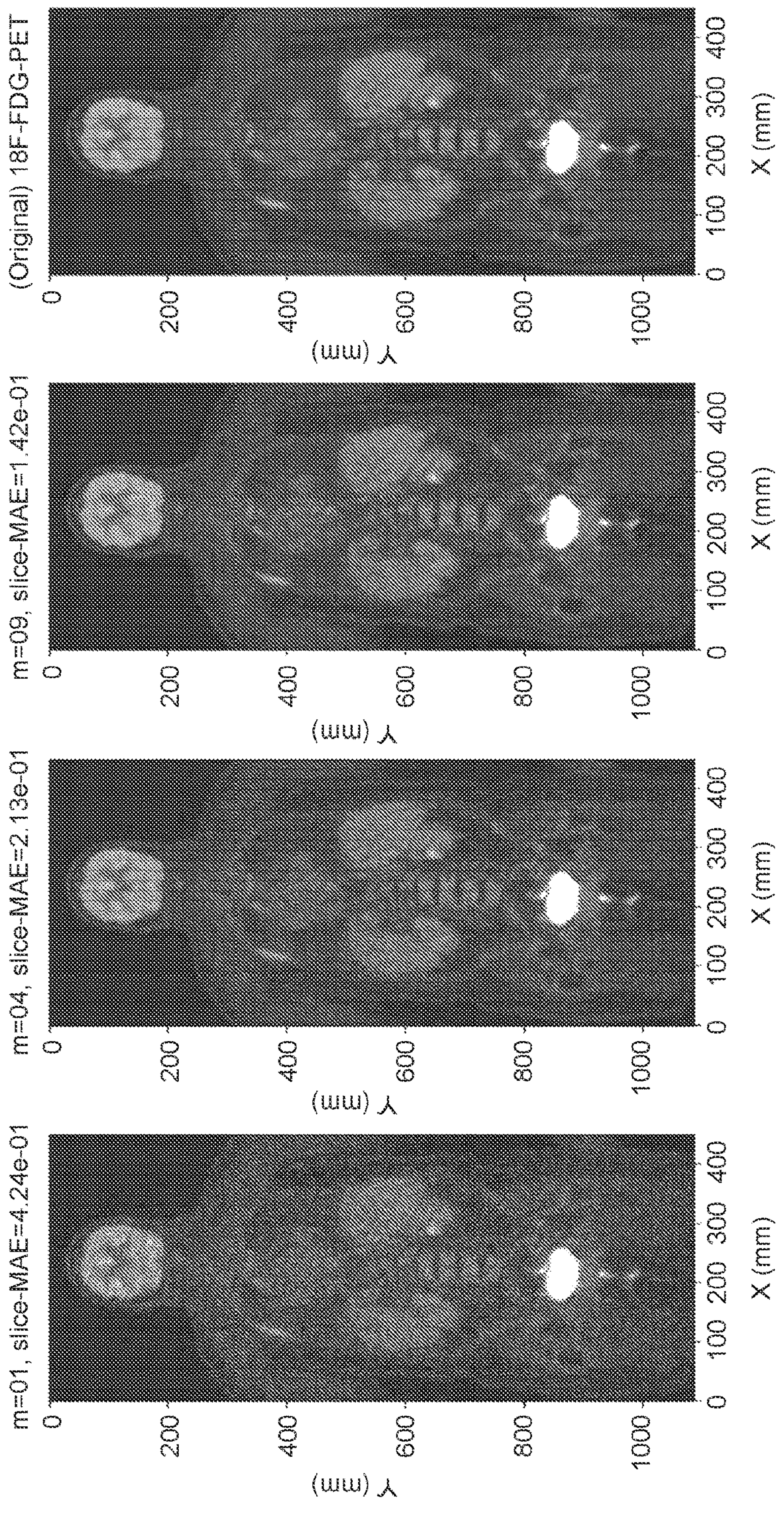
FIG. 4 shows low-dose imagery is simulated by Poisson sampling of reconstructed full-dose PET/MRI imagery.
Figure 5:
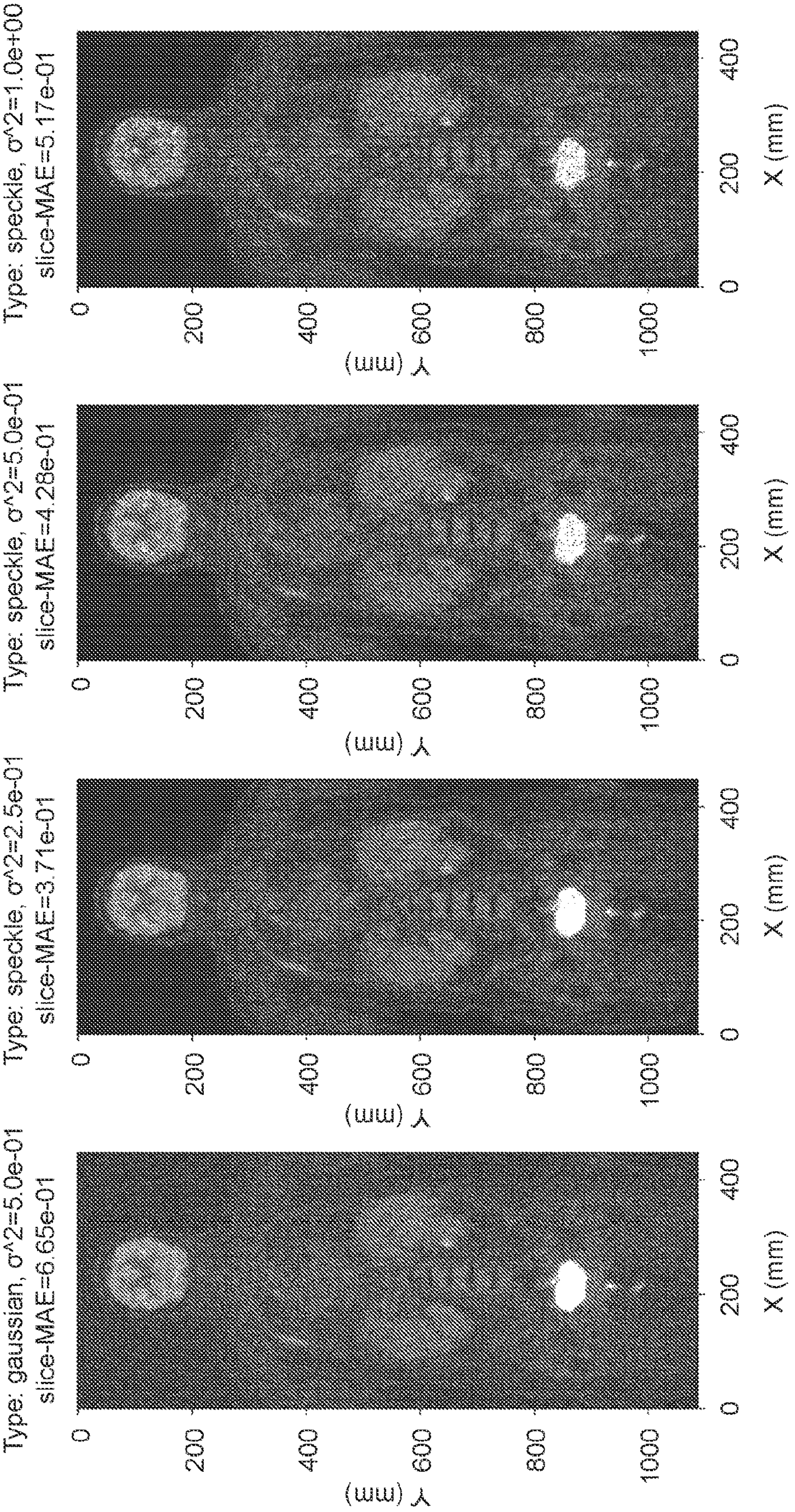
FIG. 5 shows various levels of $\alpha$=0 Gaussian and speckle noise added to simulated (m=1) volume.
Figures 6A, 6B, 6C, 6D:
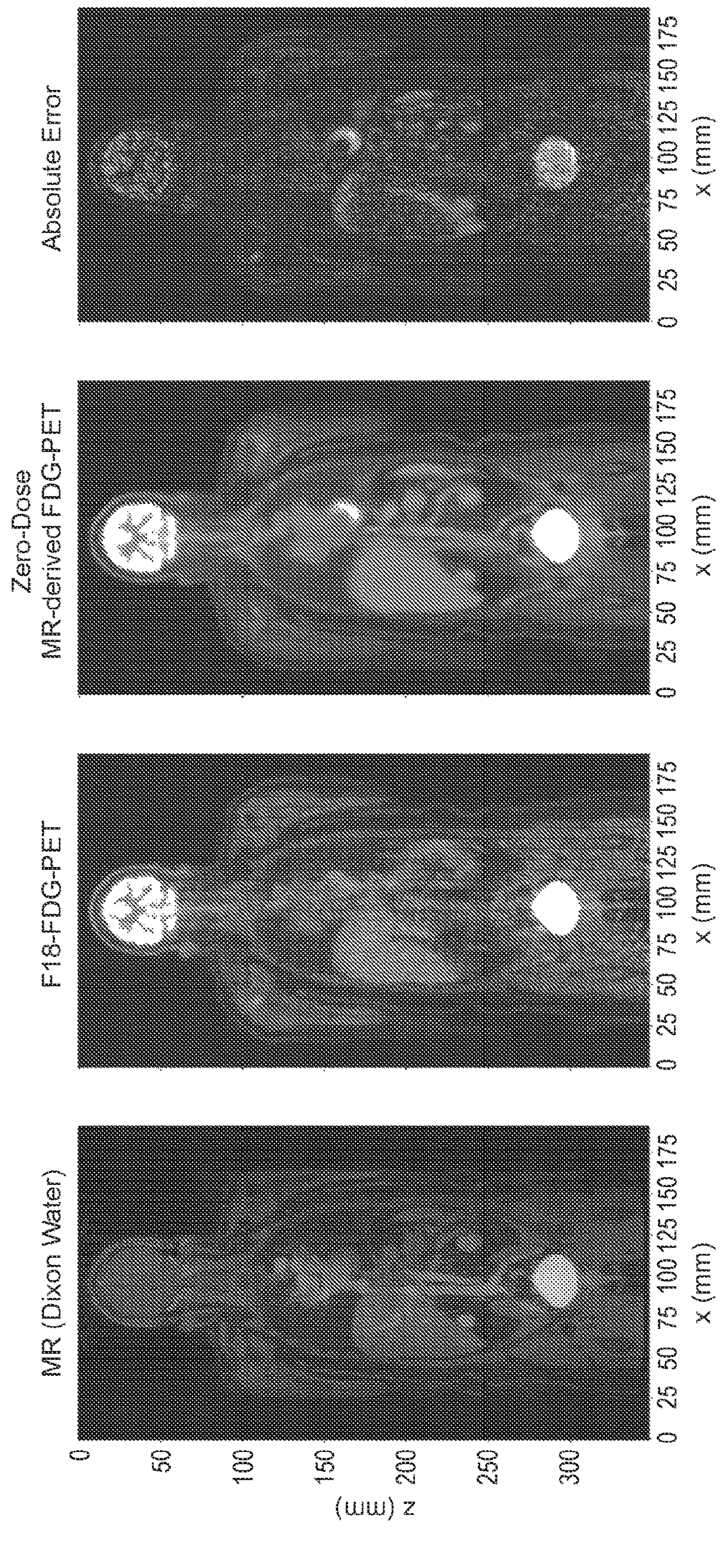
FIGS. 6A-6D show the middle coronal slices of the 3D volumes: (A) MR Dixon-Water image, (B) True FDG-PET image, (C) MR-Derived synthetic FDG-PET image, (D) absolute error, shown with the scale of [0,5] SUV.
Figure 7A:
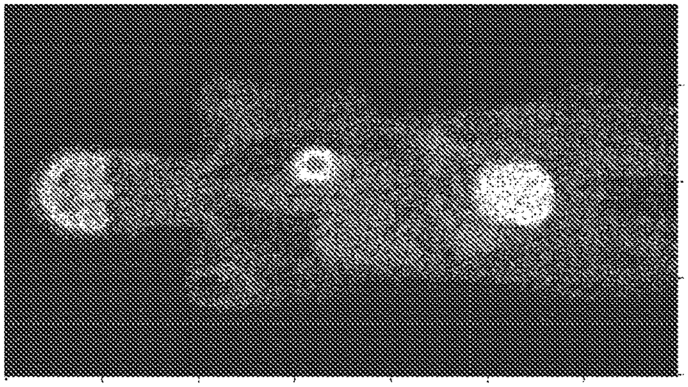
FIGS. 7A-7D show coronal slices of the 3D volumes: (A) retrospectively-simulated low-dose FDG PET, (B) MR-derived synthetic FDG-PET, (C) dichromatically-interpolated FDG-PET, and (D) full-dose F18-FDG-PET, shown with scale of [0,6] SUV.
Figure 7B:
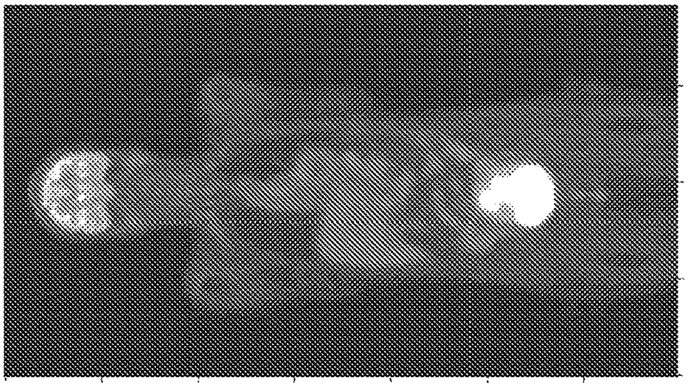
Figure 7C:
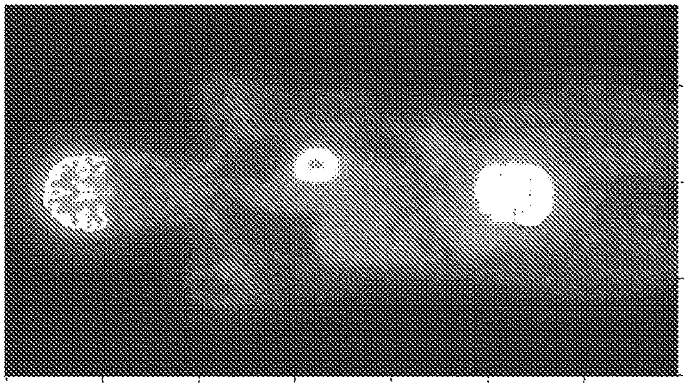
Figure 7D:
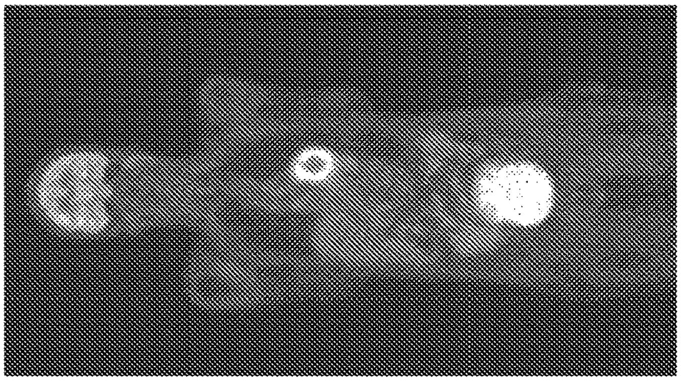

For this example, each whole-body 3D PET/MR image was sampled in a withheld test dataset of 13 exams M=10 times after and took the cumulative average after applying standardized uptake value (SUV) normalization, resulting in a low-dose PET dataset of M different noise levels for each true PET-SUV image. FIG. 4 shows the effect of sampling in the coronal plane a single exam as m={1, 4, 9}. FIG. 5 shows the effect of applying additive white Gaussian noise (AWGN) and zero-mean speckle noise to the Poisson-sampled (m=1) volumes imagery. In various tests, the reconstruction performance was compared starting with PET-SUV volumes degraded by various level of Poisson, AWGN, and speckle noise, and an (uncorrupted) T1-weighted MRI.

Results

Supervised Domain Translation of MRI (Dixon Water) to 18F-FDG-PET Volumes

Results indicate excellent agreement between the predicted MR-derived synthetic FDG-PET volumes and the true measured 18F-FDG-PET volumes, except in areas with expected dynamic activity (e.g. bladder, myocardium). An example prediction result from the test set is shown in FIGS. 6A-6D.

Enhancement of Noisy (Simulated Low-Dose) 18F-FDG-PET Imagery

Results indicate that dichromatic interpolation can successfully utilize the structural patterns in MR-derived synthetic PET to enhance statistics-limited low-dose PET imagery. As shown in FIGS. 7A-7D, the unique functional information of low-dose PET in the myocardium is fused with the anatomically-conforming synthetic PET to closely match the full-dose PET image. Structures in the brain also become more apparent and clear in the dichromatically-interpolated PET image, compared to both the low-dose and the synthetic PET images.

Figure 8:
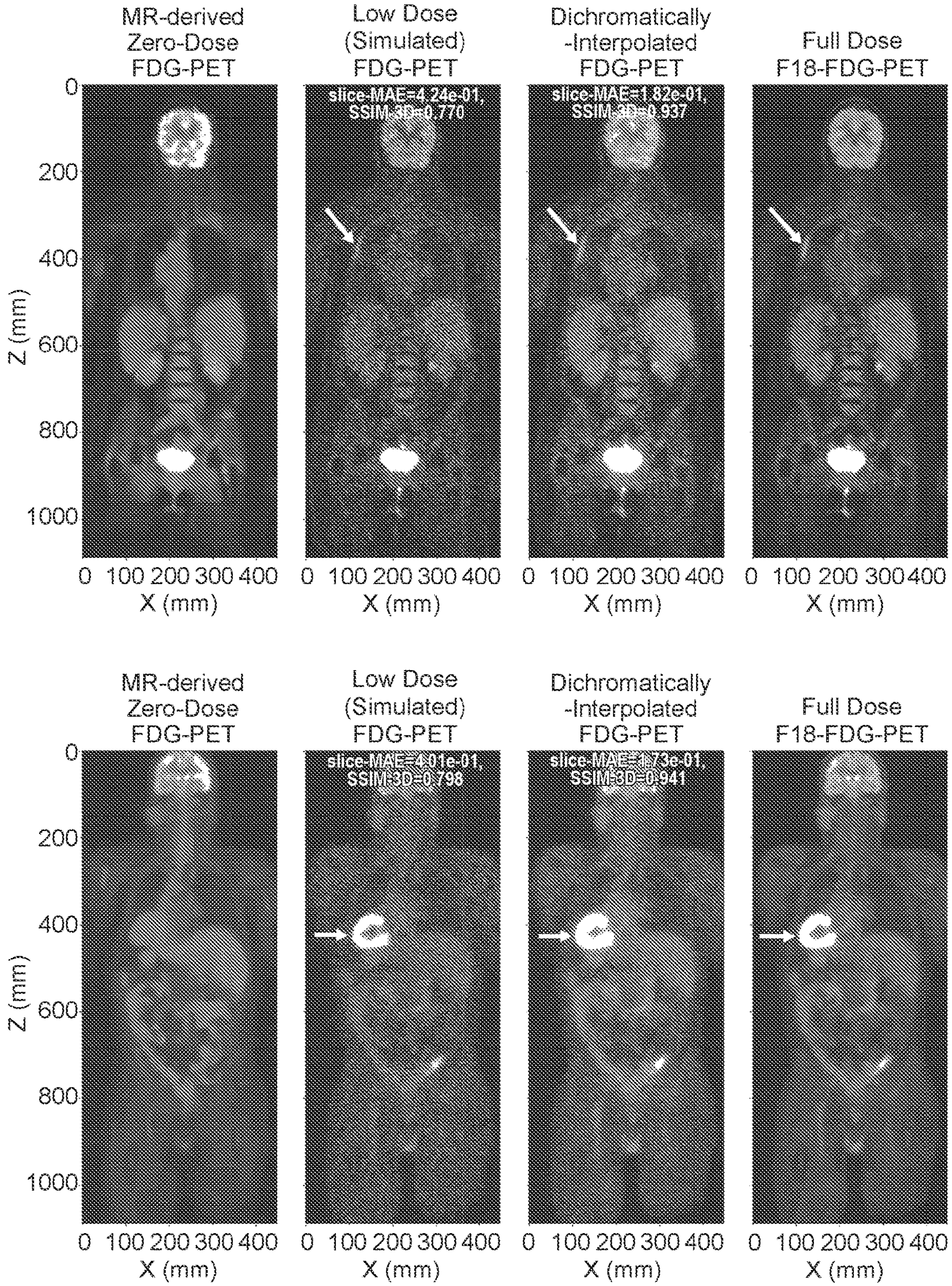
FIG. 8 shows coronal slices of the 3D volumes corresponding to MR-derived synthetic FDG-PET, simulated low-dose PET, dichromatically-interpolated PET, and full-dose F18-FDG-PET, shown with scale of [0,6] SUN. Besides improved image quality, both exams indicate an important property of dichromatic interpolation that crucially retains tracer-specific functional information even though this is missing from the synthetic PET. In the top row, what appears to be a rib metastases is retained in the dichromatically interpolated image. In the bottom row, activity in the heart is retained.
Figure 9:
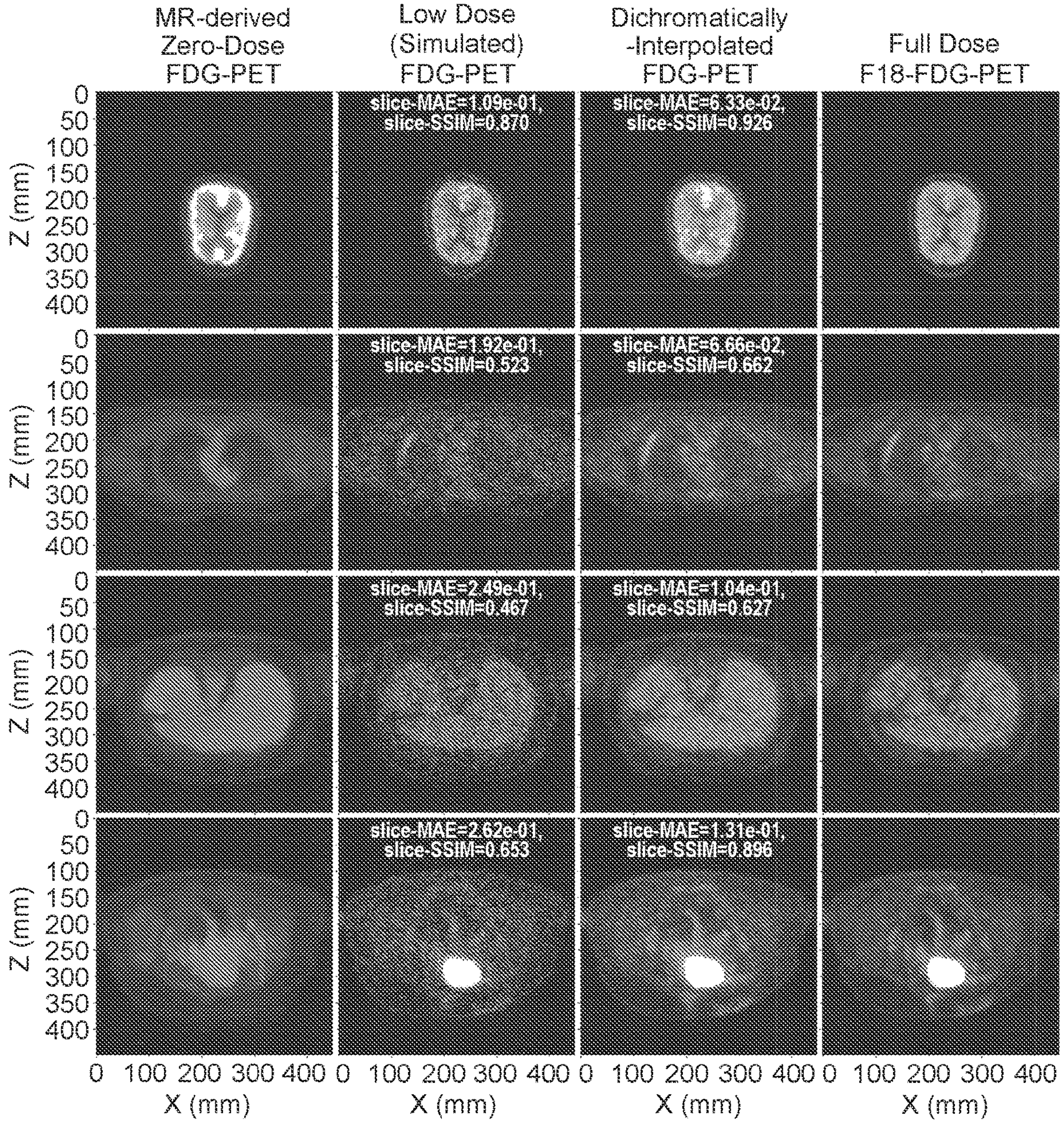
FIG. 9 shows transverse slices of the 3D volumes corresponding to simulated low-dose FDG PET, MR-derived synthetic FDG-PET, dichromatically-interpolated FDG-PET, and (full-dose F18-FDG-PET, shown with scale of [0,6] SUV.

The performance was evaluated as a function of sampling and injected noise, demonstrating that the approach consistently enhances noisy PET/MR imagery, even as the applied noise factor diminishes to zero. This is an important property that highlights the consistency of the physics-based method in the presence of different levels of noise. FIG. 8 visualizes the reconstructions in the coronal plane, while FIG. 9 visualizes improvements in the transverse plane. Numerical results comparing the mean absolute error (MAE), mean relative error (rMAE), and structural similarity index measure (SSIM), are shown in Tables 1-2. Note that all synthetic FDG-PET images used were from the test set, withheld from the training of the domain-translating 3D UNet

TABLE 1

| Image quality metrics (μ ± 1σ) on the test set compared with the full-dose 18F-FDG-PET/MRI. | | | |
|---|---|---|---|
| | MAE (SUV) | PSNR (dB) | 3D-SSIM |
| Low dose (simulated) PET | 0.1721 ± 0.0650 | 32.80 ± 3.67 | 0.673 ± 0.121 |
| Dichromatically-Interpolated PET | 0.0776 ± 0.0369 | 38.75 ± 3.53 | 0.808 ± 0.118 |

TABLE 2

| Comparison of average, min, and max improvements in image quality metrics provided by dichromatic interpolation of low-dose PET with MR-derived synthetic PET. As is seen, the minimum improvement is always positive. | | | |
|---|---|---|---|
| | MAE (SUV) | PSNR (dB) | 3D-SSIM |
| Min improvement | 0.0238(−42.9%) | 2.99(0.08%) | 0.013(1.49%) |
| Max improvement | 0.1583(−66.8%) | 6.99(23.7%) | 0.248(66.4%) |
| Average improvement | 0.0945(−56.5%) | 5.95(18.4%) | 0.135(21.8%) |

Discussion

It is notable that the image quality, as quantified through the mean absolute error (MAE) and structural similarity index measure (SSIM), strictly improves when combining the corrupted low-dose PET images with the synthetic PET images using dichromatic interpolation, with no observed failure cases. Although in some extreme cases the improvement in SSIM was very small (1.49%), the percent-improvement in MAE for those cases is still quite considerable (−42.9%). This can be further validated experimentally by evaluation using more exams with a greater variety of real and synthetically corrupted images that cover the full range of possible image phenotypes.

Of particular interest are cases where there is a stark difference in functional information between the synthetic PET and the low dose PET, such as shown in FIG. 8. In such cases, dichromatic interpolation appears to desirably improve image quality by incorporating higher-resolution gradient information from the synthetic PET, but crucially retains the FDG-specific functional information present in the low dose image. This is the intended effect, and highlights the importance of enforcing strong constraints on deep learning predictions.

Specifically, this example demonstrates the following:

Supervised domain translation of MRI to PET was performed to render physiological or otherwise expected uptake patterns, which capture the spatial structure of PET imagery using MRI without a radiation dose.

Deep learning-based domain translation was applied to the PET image reconstruction task through explicit sparsity-based regularization, rather than un-parameterized implicit regularization through deep convolutional coding. This is important, since it lets users tune the importance and properties of the regularization function to improve overall reconstruction accuracy, rather than relying on the hidden properties of CNNs that sometimes have unreliable performance on previously-unseen data.

Enhanced reconstruction performance from noisy and (retrospectively generated) low-dose PET imagery was demonstrated, even without knowledge of the PET projection/system matrix.

In particular, this example demonstrates that domain-translated PET priors can be combined with actual measurements from the target domain, can be further extended to joint-sparsity type objectives and reconstruction from measured sinogram data by incorporating a PET imaging system matrix and statistical models for scatter and random coincidence events. More broadly, the presented techniques can be applied to any image reconstruction problem utilizing deep domain translation, such as for the reconstruction of SPECT, ultrasound, or even radar.

ADDITIONAL CONSIDERATIONS

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed is:

1. A system comprising:

one or more processors; and a memory coupled to the one or more processors, the memory storing a plurality of instructions executable by the one or more processors, the plurality of instructions comprising instructions that when executed by the one or more processors cause the one or more processors to perform operations comprising:

obtaining measurement data from one or more imaging modalities;

generating a base image by solving an optimization problem using at least a signal model and the measurement data;

generating, using a deep-learning model comprising model parameters learned for reconstruction of images, a predicted image based on the measurement data;

selecting a modified operator based on physics of the optimization problem, the signal model, or a system matrix;

generating an enhanced image by solving a modified optimization problem using at least: (i) the base image or the measurement data, (ii) the signal model, (iii) the predicted image, and (iv) the modified operator; and outputting the enhanced image.

2. The system of claim 1, wherein the generating the base image comprises computing a solution to an image reconstruction problem using the signal model, the measurement data, and an unknown image to be reconstructed, computing a solution to a regularization function using the unknown image to be reconstructed, a reconstructed image, and a deep-learning derived image, comparing the solution to the image reconstruction problem and the solution to the regularization function, and determining the base image that satisfies or minimizes the optimization problem based on the comparing.

3. The system of claim 1, wherein the generating the enhanced image comprises computing a solution to an image reconstruction problem using the base image or the measurement data, the signal model, the modified operator, and an unknown image to be reconstructed, computing a solution to a regularization function by comparing the image to be reconstructed to the predicted image and the measurement data, comparing the solution to the image reconstruction problem and the solution to the regularization function, and determining the enhanced image that satisfies or minimizes the modified optimization problem based on the comparing.

4. A non-transitory computer-readable memory storing a plurality of instructions executable by one or more processors, the plurality of instructions comprising instructions that when executed by the one or more processors cause the one or more processors to perform operations comprising:

obtaining measurement data from one or more imaging modalities;

generating a base image by solving an optimization problem using at least a signal model and the measurement data;

generating, using a deep-learning model comprising model parameters learned for reconstruction of images, a predicted image based on the measurement data;

selecting a modified operator based on physics of the optimization problem, the signal model, or a system matrix;

generating an enhanced image by solving a modified optimization problem using at least: (i) the base image or the measurement data, (ii) the signal model, (iii) the predicted image, and (iv) the modified operator; and outputting the enhanced image.

5. The non-transitory computer-readable memory of claim 4, wherein the generating the base image comprises computing a solution to an image reconstruction problem using the signal model, the measurement data, and an unknown image to be reconstructed, computing a solution to a regularization function using the unknown image to be reconstructed, a reconstructed image, and a deep-learning derived image, comparing the solution to the image reconstruction problem and the solution to the regularization function, and determining the base image that satisfies or minimizes the optimization problem based on the comparing.

6. The non-transitory computer-readable memory of claim 4, wherein the generating the enhanced image comprises computing a solution to an image reconstruction problem using the base image or the measurement data, the signal model, the modified operator, and an unknown image to be reconstructed, computing a solution to a regularization function by comparing the image to be reconstructed to the predicted image and the measurement data, comparing the solution to the image reconstruction problem and the solution to the regularization function, and determining the enhanced image that satisfies or minimizes the modified optimization problem based on the comparing.

7. A method for image reconstruction, comprising:

obtaining measurement data from one or more imaging modalities;

generating a base image by solving an optimization problem using at least a signal model and the measurement data;

generating, using a deep-learning model comprising model parameters learned for reconstruction of images, a predicted image based on the measurement data;

selecting a modified operator based on physics of the optimization problem, the signal model, or a system matrix;

generating an enhanced image by solving a modified optimization problem using at least: (i) the base image or the measurement data, (ii) the signal model, (iii) the predicted image, and (iv) the modified operator; and outputting the enhanced image.

8. The method of claim 7, wherein the generating the base image comprises computing a solution to an image reconstruction problem using the signal model, the measurement data, and an unknown image to be reconstructed, computing a solution to a regularization function using the unknown image to be reconstructed, a reconstructed image, and a deep-learning derived image, comparing the solution to the image reconstruction problem and the solution to the regularization function, and determining the base image that satisfies or minimizes the optimization problem based on the comparing.

9. The method of claim 7, wherein the model parameters are learned, using a set of training data comprising a plurality of measurements associated with the one or more imaging modalities, based on minimizing a loss function.

10. The method of claim 7, wherein the generating the enhanced image comprises computing a solution to an image reconstruction problem using the base image or the measurement data, the signal model, the modified operator, and an unknown image to be reconstructed, computing a solution to a regularization function by comparing the image to be reconstructed to the predicted image and the measurement data, comparing the solution to the image reconstruction problem and the solution to the regularization function, and determining the enhanced image that satisfies or minimizes the modified optimization problem based on the comparing.

11. The method of claim 7, wherein the modified optimization problem is of the form:

$$\hat{x}_{enhanced} = \min_{x}\left|\tilde{A}x - \hat{x}_{conventional}\right| + R_{DL}(x, \hat{x}_{DL}, b)$$

where $\tilde{A}$ is the modified operator, x is the image to be reconstructed, $\hat{x}_{conventional}$ is the base image or the measurement data, $R_{DL}$ is the regularization function, $\hat{x}_{DL}$ is the predicted image, and b is the measurement data.

12. The method of claim 7, further comprising determining a diagnosis or prognosis of a subject based on the enhanced image.

13. The method of claim 7, further comprising detecting, characterizing, and/or classifying, by a data processing system, a tissue within the enhanced image.

14. The method of claim 12, wherein the base image is a noisy reconstructed positron emission tomography (PET) image, and the predicted image is a synthetic PET image.

15. The method of claim 7, further comprising autonomously operating a vehicle based on the enhanced image.

16. The method of claim 15, wherein the base image is a noisy and sparse reconstructed LiDAR depth image, formed using a number of sensors, and the predicted image is a predicted depth image, reconstructed using deep learning on optical (RGB) images.

17. The method of claim 7, further comprising generating a 3D reconstruction of terrain and buildings based on the enhanced image.

18. The method of claim 17, wherein the base image is a noisy reconstructed image of buildings based on radar and the predicted image is a predicted building mask reconstructed using deep learning of optical imagery.

19. The method of claim 7, further comprising identifying an object in the enhanced image or classifying, by a machine-learning model, an object within the enhanced image.

20. The method of claim 19, wherein the base image is a noisy reconstructed image of buildings based on radar, and the predicted image is a predicted building mask, based on deep learning of optical imagery.

* * * * *